(12) United States Patent
Chen et al.

(10) Patent No.: US 11,408,127 B2
(45) Date of Patent: Aug. 9, 2022

(54) ZWITTERIONIC IMIDAZOLINIUM SURFACTANT AND USE IN THE MANUFACTURE OF ABSORBENT PAPER

(71) Applicant: GPCP IP Holdings LLC, Atlanta, GA (US)

(72) Inventors: Yu Chen, Appleton, WI (US); Brian S. Hammes, Appleton, WI (US)

(73) Assignee: GPCP IP Holdings LLC, Atlanta, GA (US)

( * ) Notice: Subject to any disclaimer, the term of this patent is extended or adjusted under 35 U.S.C. 154(b) by 176 days.

(21) Appl. No.: 16/878,819

(22) Filed: May 20, 2020

(65) Prior Publication Data

US 2020/0283960 A1    Sep. 10, 2020

Related U.S. Application Data

(62) Division of application No. 15/865,353, filed on Jan. 9, 2018, now Pat. No. 10,697,123.

(60) Provisional application No. 62/446,892, filed on Jan. 17, 2017.

(51) Int. Cl.

| | |
|---|---|
| *D21H 21/24* | (2006.01) |
| *D21H 21/20* | (2006.01) |
| *D21H 17/07* | (2006.01) |
| *C07D 233/16* | (2006.01) |
| *D21H 17/20* | (2006.01) |
| *D21H 27/00* | (2006.01) |
| *D21H 17/14* | (2006.01) |
| *D21H 17/37* | (2006.01) |
| *D21H 21/18* | (2006.01) |
| *D21H 21/22* | (2006.01) |
| *D21H 17/06* | (2006.01) |
| *D21H 17/00* | (2006.01) |
| *D21H 23/06* | (2006.01) |

(52) U.S. Cl.
CPC ........... *D21H 21/24* (2013.01); *C07D 233/16* (2013.01); *D21H 17/06* (2013.01); *D21H 17/07* (2013.01); *D21H 17/14* (2013.01); *D21H 17/20* (2013.01); *D21H 17/375* (2013.01); *D21H 17/72* (2013.01); *D21H 21/18* (2013.01); *D21H 21/20* (2013.01); *D21H 21/22* (2013.01); *D21H 23/06* (2013.01); *D21H 27/002* (2013.01)

(58) Field of Classification Search
CPC ...... D21H 21/22; D21H 17/72; D21H 27/002; D21H 17/07; D21H 21/18; D21H 17/375; D21H 17/20; D21H 17/14; D21H 21/20; D21H 17/06; D21H 23/06; D21H 21/24; C07D 233/16
USPC ........................................................ 162/158
See application file for complete search history.

(56) References Cited

U.S. PATENT DOCUMENTS

| | | |
|---|---|---|
| RE23,227 E | 5/1950 | Blair et al. |
| 2,713,582 A | 7/1955 | Smith |
| 3,556,932 A | 1/1971 | Coscia et al. |
| 3,556,933 A | 1/1971 | Williams et al. |
| 3,686,025 A | 8/1972 | Morton |
| 3,700,623 A | 10/1972 | Keim |
| 3,749,691 A | 7/1973 | Kandathil |
| 3,755,220 A | 8/1973 | Freimark et al. |
| 3,772,076 A | 11/1973 | Keim |
| 3,849,435 A | 11/1974 | Diery et al. |
| 3,994,771 A | 11/1976 | Morgan, Jr. et al. |
| 4,102,737 A | 7/1978 | Morton |
| 4,181,634 A | 1/1980 | Kennedy et al. |
| 4,254,255 A | 3/1981 | Löbach et al. |
| 4,265,810 A | 5/1981 | Bauman et al. |
| 4,351,699 A | 9/1982 | Osborn, III |
| 4,362,737 A | 12/1982 | Schafer et al. |
| 4,374,737 A | 2/1983 | Larson et al. |
| 4,441,962 A | 4/1984 | Osborn, III |
| 4,447,294 A | 5/1984 | Osborn, III |
| 4,529,480 A | 7/1985 | Trokhan |
| 4,529,803 A | 7/1985 | Tomalia et al. |
| 4,544,756 A | 10/1985 | Patel |
| 4,603,176 A | 7/1986 | Bjorkquist et al. |
| 4,675,394 A | 6/1987 | Solarek et al. |

(Continued)

FOREIGN PATENT DOCUMENTS

| | | |
|---|---|---|
| JP | H01144496 A | 6/1989 |
| JP | H07252800 A | 10/1995 |

(Continued)

OTHER PUBLICATIONS

D. Bajpai, et al., Fatty Imidazolines: Chemistry, Synthesis, Properties and Their Industrial Applications, Journal of Oleo Science, 2006, pp. 319-329, vol. 55, No. 7.

C.M. Latham et al., Short Synthesis of Chiral 4-Substituted (S)-Imidazolinium Salts Bearing Sulfonates and Their Use in γ-Selective Reactions of Allylic Halides with Grignard Reagents, European Journal of Organic Chemistry, Feb. 2012, pp. 699-707, vol. 2012, Issue 4, WILEY-VCH Verlag GmbH & Co. KGaA, Weinheim.

(Continued)

*Primary Examiner* — Mark Halpern

(57) ABSTRACT

Zwitterionic surfactant compounds and their use in connection with absorbent paper manufacture in debonder and softener formulations. An exemplary surfactant is an imidazolinium compound of formula:

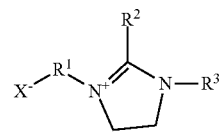

wherein X is $SO_3$, $R^1$ is a hydrocarbyl spacer group having a chain length of from 2-6 carbon atoms, $R^2$ is a hydrocarbyl group having from 8 to 22 carbon atoms; and $R^3$ is an alkenylamidoalkyl moiety having from 8 to 30 carbon atoms.

18 Claims, 5 Drawing Sheets

(56) References Cited

U.S. PATENT DOCUMENTS

| | | | |
|---|---|---|---|
| 4,786,421 | A | 11/1988 | Butterworth et al. |
| 4,804,769 | A | 2/1989 | Solarek et al. |
| 4,866,151 | A | 9/1989 | Tsai et al. |
| 4,892,555 | A | 1/1990 | Leigh et al. |
| 4,959,125 | A | 9/1990 | Spendel |
| 4,981,557 | A | 1/1991 | Bjorkquist |
| 4,983,748 | A | 1/1991 | Tsai et al. |
| 5,008,344 | A | 4/1991 | Bjorkquist |
| 5,049,315 | A | 9/1991 | Hitz et al. |
| 5,085,736 | A | 2/1992 | Bjorkquist |
| 5,138,002 | A | 8/1992 | Bjorkquist |
| 5,151,522 | A | 9/1992 | Hitz et al. |
| 5,217,576 | A | 6/1993 | Van Phan |
| 5,240,562 | A | 8/1993 | Phan et al. |
| 5,279,767 | A | 1/1994 | Phan et al. |
| 5,420,315 | A | 5/1995 | Uhrig et al. |
| 5,536,504 | A | 7/1996 | Eugster et al. |
| 5,593,691 | A | 1/1997 | Eugster et al. |
| 5,622,597 | A | 4/1997 | Callen et al. |
| 5,643,498 | A | 7/1997 | Li et al. |
| 5,698,076 | A | 12/1997 | Phan et al. |
| 5,730,839 | A | 3/1998 | Wendt et al. |
| 5,753,079 | A | 5/1998 | Jenny et al. |
| 6,176,972 | B1 | 1/2001 | Oriaran et al. |
| 6,180,661 | B1 | 1/2001 | Eugster et al. |
| 6,211,139 | B1 | 4/2001 | Keys et al. |
| 6,245,197 | B1 | 6/2001 | Oriaran et al. |
| 6,346,169 | B1 | 2/2002 | Ikeda et al. |
| 6,458,343 | B1 | 10/2002 | Zeman et al. |
| 6,623,746 | B1 | 9/2003 | Wadle et al. |
| 6,649,024 | B2 | 11/2003 | Oriarian et al. |
| 6,680,286 | B1 | 1/2004 | Kawaguchi et al. |
| 6,969,443 | B1 | 11/2005 | Kokko |
| 7,183,250 | B2 | 2/2007 | Rodrigues et al. |
| 7,585,388 | B2 | 9/2009 | Yeh et al. |
| 7,585,389 | B2 | 9/2009 | Yeh et al. |
| 7,585,494 | B2 | 9/2009 | Lange et al. |
| 7,662,257 | B2 | 2/2010 | Edwards et al. |
| 7,682,488 | B2 | 3/2010 | Yeh et al. |
| 7,736,464 | B2 | 6/2010 | Kokko |
| 7,850,823 | B2 | 12/2010 | Chou et al. |
| 7,951,266 | B2 | 5/2011 | Kokko et al. |
| 8,778,138 | B2 | 7/2014 | Super et al. |
| 8,852,399 | B2 | 10/2014 | Neal et al. |
| 9,506,201 | B2 | 11/2016 | Furman et al. |
| 10,016,354 | B2 | 7/2018 | Konradi et al. |
| 10,669,673 | B2 | 6/2020 | Chen et al. |
| 10,697,123 | B2 | 6/2020 | Chen et al. |
| 2003/0056917 | A1 | 3/2003 | Jimenez |
| 2004/0163182 | A1 | 8/2004 | Nguyen |
| 2004/0259758 | A1 | 12/2004 | Rodrigues et al. |
| 2005/0119146 | A1 | 6/2005 | Rodrigues |
| 2006/0060319 | A1 | 3/2006 | Kokko |
| 2007/0107863 | A1 | 5/2007 | Edwards et al. |
| 2007/0224419 | A1 | 9/2007 | Sumnicht et al. |
| 2009/0020248 | A1 | 1/2009 | Sumnicht |
| 2012/0045611 | A1 | 2/2012 | Shih et al. |
| 2012/0244095 | A1 | 9/2012 | Konradi et al. |
| 2018/0202108 | A1 | 7/2018 | Chen et al. |
| 2018/0202109 | A1 | 7/2018 | Chen et al. |
| 2018/0296459 | A1 | 10/2018 | Konradi et al. |
| 2020/0199819 | A1 | 6/2020 | Chen et al. |

FOREIGN PATENT DOCUMENTS

| | | |
|---|---|---|
| JP | 2003171871 A | 6/2003 |
| WO | 1998049898 A1 | 11/1998 |
| WO | 2017151084 A1 | 9/2017 |
| WO | 2018136318 A1 | 7/2018 |

OTHER PUBLICATIONS

Espy, Chapter 2: Alkaline-Curing Polymeric Amine-Epichlorohydrin Resins, Wet-Strength Resins and Their Application (L. Chan, Ed.), 1994, pp. 13-44.

Westfelt, Chemistry of Paper Wet-Strength, I. A Survey of Mechanisms of Wet Strength Development, Cellulose Chemistry and Technology, 1979, pp. 813-825, vol. 13.

Strazdins, Chapter 4: Application of Electrokinetics in Optimization of Wet-End Chemistry, Wet-Strength Resins and Their Application (L. Chan, Ed.), pp. 63-83, 1994.

International Search Report and Written Opinion in corresponding PCT/US2018/013046 dated May 8, 2018.

International Search Report and Written Opinion in PCT/US2018/013457 dated May 8, 2018.

Sheshenev, et al., New Chiral Zwitterionic Phosphorus Heterocycles: Synthesis, Structure, Properties and Application as Chiral Solvating Agents, Chemistry, A European Journal, 2013, pp. 8136-8143, vol. 19, Issue 25, Wiley-VCH Verlag GmbH & Co. KGaA, Weinheim.

PUBCHEM-CID 74935089 Create Date: Jul. 1, 2014, pp. 1-11.

International Preliminary Report on Patentability in corresponding PCT/US2018/013046 dated Oct. 22, 2018.

Tsumadori, M. "Recent Trends of Surfactants in the Fabric & Home Care Field" CD Proceedings 6th World Surfactant Congress CESIO, Berlin Germany, paper# 196, Jun. 21-23, 2004, pp. 1-6.

International Preliminary Report on Patentability in related PCT/US2018/013457 dated Oct. 4, 2018.

Non Final office action received for U.S. Appl. No. 16/806,036, dated Apr. 1, 2022, 11 Pages.

Stepan. Imidazolinium, Softener Data Sheet. (Year: 2022), 3 Pages.

TENSILE REDUCTION VS. DEBONDER DOSAGE

WET/DRY TENSILE (%)

TENSILE REDUCTION VS. DEBONDER DOSAGE

WET/DRY TENSILE (%)

DRY TENSILE VS. DEBONDER DOSAGE

TENSILE REDUCTION VS. DEBONDER DOSAGE

ZWITTERIONIC IMIDAZOLINIUM SURFACTANT AND USE IN THE MANUFACTURE OF ABSORBENT PAPER

CLAIM FOR PRIORITY

This application is a divisional application of U.S. patent application Ser. No. 15/865,353, filed Jan. 9, 2018 of the same title. Application Ser. No. 15/865,353 is based on U.S. Provisional Application No. 62/446,892, filed Jan. 17, 2017, also entitled *Zwitterionic Imidazolinium Surfactant and Use in the Manufacture of Absorbent Paper*. The priorities of the foregoing applications are hereby claimed and their disclosures incorporated herein by reference.

TECHNICAL FIELD

The present invention relates to zwitterionic imidazolinium surfactant compounds useful for debonder and/or softener compositions utilized in manufacture of absorbent sheet such as paper tissue or paper towel.

BACKGROUND

Zwitterionic compounds and surfactants are known in the art. See Christopher M. Latham et al., Short Synthesis of Chiral 4-Substituted (S)-Imidazolinium Bearing Sulfonates and Their Use in γ-Selective Reactions of Allylic Halides with Grignard Reagents, European Journal of Organic Chemistry Volume 2012, Issue 4, pages 699-707, February 2012. U.S. Pat. No. 6,346,169 to Ikeda et al. discloses and claims a paper bulking promoter comprising amphoteric compounds. Note structure j3, which is an imidazolinium carboxylate. Notably, the amphoteric compounds disclosed do not appear to operate as debonders, Col. 2, lines 38-48. Note, also, U.S. Pat. No. 6,623,746 to Wadle et al. which discloses a variety of zwitterionic surfactants at Col. 6, lines 31 and following.

Debonder compositions are widely used in connection with the manufacture of absorbent paper products such as paper tissue and paper towel to adjust tensile strength and provide softness. Among the most effective compounds are quaternary ammonium surfactants which are sometimes used together with nonionic surfactants. Debonders are used with numerous additives such as wet strength agents and so forth. See U.S. Pat. No. 3,755,220 to Freimark et al. (1973), Col. 2, lines 1-10. U.S. Pat. No. 6,969,443 to Kokko discloses debonder compositions, including imidazolium salts in combination with nonionic surfactants. This reference also discloses the use of additives, including charge modifiers, wet strength resins, retention aids and auxiliaries such as carboxymethylcellulose. See Cols. 10-12. So also, U.S. Pat. No. 6,649,024 to Oriarian et al. discloses absorbent products incorporating a variety of cationic debonders, including di- or trialkyl ammonium salts. United States Patent Application Publication No. US2004/0163182 to Nguyen discloses nonionic surfactants used in combination with amide substituted imidazolinium salts. See paragraph [0013]. U.S. Pat. No. 4,959,125 to Spendel (1990) discloses manufacture of absorbent sheet with ampholytic or zwitterionic surfactants. See Col. 11, lines 21-46.

U.S. Pat. No. 3,686,025 to Morton (1972) discloses the use of quaternary imidazolinium salts with acyclic zwitterionic quaternary ammonium surfactants. Acyclic zwitterionic quaternary ammonium surfactants tend to be high foaming compounds which are useful for soaps/bath products; typically made with a single hydrophobic long chain which are not generally very effective as debonders in paper manufacture. Biodegradability of such compounds is also poor, making them especially undesirable for bath tissue which inevitably finds its way to septic systems.

A significant drawback of conventional systems using quaternary ammonium salts is that these compounds contribute significantly to titratable charge and change zeta potential. Controlling charge and zeta potential of the furnish in the headbox is critical to papermachine performance, especially retention of papermaking solids in the final product. The problem with adding too much cationic additive is that it will exceed the adsorption capacity of the fiber surfaces, based on either the surface area or the limited extent of negative charge of the surfaces of fibers and other solid surfaces in the furnish. Excess cationic additives beyond what adheres to the fibers is likely to cause foam, high biological oxygen demand (BOD) levels in the effluent, and poor retention and drainage. Conventional charge control agents such as carboxymethyl cellulose can adversely impact softness of the product. The use of charge control agents may be reduced or even avoided entirely when using the compositions of the present invention.

SUMMARY OF INVENTION

There is provided in accordance with the invention zwitterionic surfactant compounds and their use in connection with absorbent paper manufacture. In general, surfactant compounds of the invention are imidazolinium compounds of the formula:

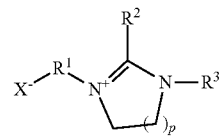

wherein X is $SO_3$ or other suitable anionic moiety such as $CO_2$, $PO_3$ and $HPO_2$; $R^1$ is a spacer group bearing the anionic moiety; $R^2$ and $R^3$ are generally hydrophobic substituents having from 3 to 30, typically 8 to 22 carbon atoms; and p is 1 or 2. The surfactant illustrated may be further substituted if so desired. Suitable further substituents might include one or more groups which can be the same or different and are independently selected from the group consisting of halogen, cyano, alkyl, cycloalkyl, —OH, $O(C_1\text{-}C_6)$ alkyl, —C(=O)$(C_1\text{-}C_6)$ alkyl, —$CO_2H$, —C(=O)O$(C_1\text{-}C_6)$ alkyl, N[$(C_1\text{-}C_6)$ alkyl]$_2$, and —NH [$(C_1\text{-}C_6)$ alkyl].

The surfactants of the invention are surprisingly effective as debonders when used in connection with cationic permanent or cationic temporary wet strength resins as hereinafter demonstrated.

The compositions of the invention also provide unexpected effectiveness in controlling charge in the furnish over a wide range of addition, especially as seen in connection with titratable charge and zeta potential when employing compositions of the invention. The invention thus provides for high levels of debonder addition without consuming anionic charge of papermaking fibers, enabling higher levels of addition of other cationic additives such as retention aids and the like without compromising softness of the product by requiring cellulosic charge control agents.

Further features and advantages will become apparent from the discussion which follows.

BRIEF DESCRIPTION OF DRAWINGS

The invention is described in detail below with reference to the drawings wherein.

DETAILED DESCRIPTION

Figure 1A:
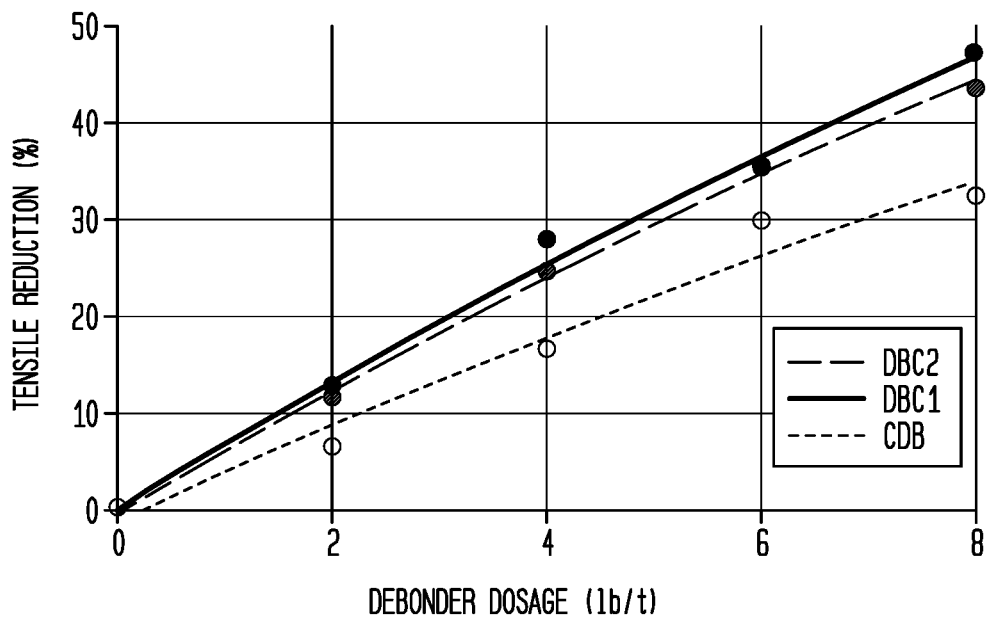
FIG. 1A is a plot of tensile reduction versus debonder dosage for handsheets, wherein the furnish was treated with cationic permanent wet strength resin prior to adding debonder.

The invention is described in detail below in connection with the Figures for purposes of illustration only. The invention is defined in the appended claims. Terminology used herein is given its ordinary meaning consistent with the exemplary definitions set forth immediately below; g refers to grams, $m^2$ refers to square meters, percents, ppm and like terminology relates to weight percent, parts per million by weight and so forth.

Add-on of various components in lbs/ton is expressed in lbs additive per ton of air dry pulp or papermaking fibers.

"Alkyl" means an aliphatic hydrocarbon group which may be straight or branched and comprising about 1 to about 30 carbon atoms in the chain. Branched means that one or more groups are attached to a linear alkyl chain. Alkyl may be unsubstituted or optionally substituted by one or more substituents which may be the same or different, each substituent being independently selected from the group as defined.

"Alkenyl" means an aliphatic hydrocarbon group containing at least one carbon-carbon double bond and which may be straight or branched and comprising about 2 to about 30 carbon atoms in the chain. Branched means that one or more groups are attached to a linear alkenyl chain. Alkenyl may be unsubstituted or optionally substituted by one or more substituents which may be the same or different, each substituent being independently selected from the group as defined.

"Cycloalkyl" means a non-aromatic mono- or multicyclic ring system comprising about 3 to about 10 carbon atoms, preferably about 5 to about 10 carbon atoms. The cycloalkyl can be optionally substituted with one or more substituents which may be the same or different, each substituent being independently selected from the group as defined.

When we refer to a hydrocarbyl group or hydrocarbon moiety having interposed within it one or more groups such as —NH—C(O)—, —C(O)—NH—, —O—, —SO$_2$—, —C(=O)— and the like we refer to ether, amide, sulfone, ketone moieties and the like forming part of the chain such as ethylene oxide within the hydrocarbon chain.

"Consisting essentially of" and like terminology refers to the recited components and excludes other ingredients which would substantially change the basic and novel characteristics of the composition or article. Unless otherwise indicated or readily apparent, a composition or article consists essentially of the recited or listed components when the composition or article includes 90% or more by weight of the recited or listed components. That is, the terminology excludes more than 10% unrecited components.

Cationic Wet Strength Resins

Permanent and temporary cationic wet strength resins are often incorporated into tissue and towel absorbent paper products. Of particular utility for permanent wet strength resins are the polyamidoamine-epichlorohydrin wet strength resins, examples of which are sold under the trade names Amres® from Georgia-Pacific Resins, Inc. and Kymene™ 557LX and Kymene™ 557H by Hercules Incorporated of Wilmington, Del. These resins and the process for making the resins are described in U.S. Pat. Nos. 3,700,623 and 3,772,076. An extensive description of polymeric-epihalohydrin resins is given in Chapter 2: *Alkaline-Curing Polymeric Amine-Epichlorohydrin* by Espy in *Wet Strength Resins and Their Application*, pp. 13-44 (L. Chan, Editor, 1994). A reasonably comprehensive list of wet strength resins is described by Westfelt in *Cellulose Chemistry and Technology* Volume 13, pp. 813-825, 1979.

Temporary cationic wet strength resin may be any one of a variety of water-soluble organic polymers comprising aldehydic units and cationic units used to increase dry and wet tensile strength of a paper product. Such resins are described in U.S. Pat. Nos. 4,675,394; 5,240,562; 5,138,002; 5,085,736; 4,981,557; 5,008,344; 4,603,176; 4,983,748; 4,866,151; 4,804,769 and 5,217,576. Modified starches sold under the trademarks CO-BOND® 1000 and CO-BOND® 1000 Plus, by National Starch and Chemical Company of Bridgewater, N.J. may be used. Prior to use, the cationic aldehydic water soluble polymer can be prepared by preheating an aqueous slurry of approximately 5% solids maintained at a temperature of approximately 240° F. and a pH of about 2.7 for approximately 3.5 minutes. Finally, the slurry can be quenched and diluted by adding water to produce a mixture of approximately 1.0% solids at less than about 130° F.

Temporary wet strength agents of glyoxylated polyacrylamide resins are commonly produced by reacting acrylamide with diallyl dimethyl ammonium chloride (DADMAC) to produce a cationic polyacrylamide copolymer which is ultimately reacted with glyoxal to produce a cationic cross-linking temporary or semi-permanent wet strength resin, glyoxylated polyacrylamide. These materials are generally described in U.S. Pat. No. 3,556,932 to Coscia et al. and U.S. Pat. No. 3,556,933 to Williams et al. Resins of this type are commercially available under the trade name of Kemira Fennorez® 110 or PAREZ 631NC (Cytec). Different mole ratios of acrylamide/DADMAC/glyoxal can be used to produce cross-linking resins, which are useful as wet strength agents. Furthermore, other dialdehydes can be substituted for glyoxal to produce wet strength characteristics.

Cellulosic Sheet, Components and Related Terminology

The term "cellulosic", "cellulosic sheet" and the like are meant to include any product incorporating papermaking fiber having cellulose as a major constituent. "Papermaking fibers" include virgin pulps or recycle (secondary) cellulosic fibers or fiber mixes comprising cellulosic fibers. Fibers suitable for making the webs of this invention include: nonwood fibers, such as cotton fibers or cotton derivatives, abaca, kenaf, sabai grass, flax, esparto grass, straw, jute hemp, bagasse, milkweed floss fibers, and pineapple leaf fibers; and wood fibers such as those obtained from deciduous and coniferous trees, including softwood fibers, such as northern and southern softwood Kraft fibers; hardwood fibers, such as eucalyptus, maple, birch, aspen, or the like. Papermaking fibers used in connection with the invention are typically naturally occurring pulp-derived fibers (as opposed to reconstituted fibers such as lyocell or rayon) which are liberated from their source material by any one of a number of pulping processes familiar to one experienced in the art including sulfate, sulfite, polysulfide, soda pulping, etc. The pulp can be bleached if desired by chemical means including the use of chlorine dioxide, oxygen, alkaline peroxide and so forth. The products of the present invention may comprise a blend of conventional fibers (whether derived from virgin pulp or recycle sources) and high coarseness lignin-rich tubular fibers, such as bleached chemical thermomechanical pulp (BCTMP). Pulp-derived fibers thus also include high yield fibers such as BCTMP as well as thermomechanical pulp (TMP), chemithermomechanical pulp (CTMP) and alkaline peroxide mechanical pulp (APMP). "Furnishes" and like terminology refers to aqueous compositions including papermaking fibers, optionally wet strength resins, debonders and the like for making paper products.

Kraft softwood fiber is low yield fiber made by the well known Kraft (sulfate) pulping process from coniferous material and includes northern and southern softwood Kraft fiber, Douglas fir Kraft fiber and so forth. Kraft softwood fibers generally have a lignin content of less than 5 percent by weight, a length weighted average fiber length of greater than 2 mm, as well as an arithmetic average fiber length of greater than 0.6 mm.

Kraft hardwood fiber is made by the Kraft process from hardwood sources, i.e., eucalyptus and also has generally a lignin content of less than 5 percent by weight. Kraft hardwood fibers are shorter than softwood fibers, typically having a length weighted average fiber length of less than 1 mm and an arithmetic average length of less than 0.5 mm or less than 0.4 mm.

Recycle fiber may be added to the papermaking furnish in any amount. While any suitable recycle fiber may be used, recycle fiber with relatively low levels of ground wood is preferred in many cases, for example recycle fiber with less than 15% by weight lignin content, or less than 10% by weight lignin content, may be preferred depending on the furnish mixture employed and the application. Recycle fiber is in many cases 80% hardwood fiber.

Zeta potential and titratable charge of the furnish are measured as described in U.S. Pat. No. 7,682,488 to Yeh et al. Details on both the electrophoretic mobility and titratable charge techniques can be found in Principles of Colloid and Surface Chemistry by P. Hiemenz and in Chapter 4: *Application of Electro kinetics in Optimization of Wet End Chemistry* in Wet Strength Resins and Their Application (L. Chan, Editor, 1994). In particular, a furnish slurry is tested for titratable charge with either a 0.001 N solution of PolyDADMAC or PVSK using a Mutek as titratable charge detector. The salvageable components are recombined with the treated slurry and tested for zeta-potential with a Mutek SZP-10.

"Basesheet" refers to a unitary cellulosic sheet as manufactured by a paper machine. Basesheets may be layered; however, they have a unitary structure not readily delaminated. A "ply" of a finished product refers to basesheet incorporated into the product.

Unless otherwise specified, "basis weight", BWT, bwt, and so forth refers to the weight of a sheet product per specified area.

Consistency refers to percent solids of a nascent web, for example, calculated on a bone dry basis. A nascent web having 50 percent water and 50 percent bone dry pulp has a consistency of 50 percent.

"Air dry" or simply "dry" means including residual moisture, by convention up to about 10 percent moisture for pulp and up to about 6 percent for paper; while oven dry refers to pulp or paper which is dried in an oven for several hours and is significantly drier.

Products of the invention are made with a cellulosic fiber basesheet and have an absorbency or SAT value as well as tensiles and densities suitable for tissue and towel products. Typical SAT values are greater than about 3 g/g in most cases. See U.S. Pat. No. 8,778,138.

"CWP" refers to a process for making absorbent products by way of a conventional wet-press process; that is, wet-pressing a furnish to a drying cylinder with a papermaking felt followed by creping the web from the cylinder. See U.S. Pat. No. 7,951,266, FIG. 7 thereof.

A "Structured Basesheet Process" refers to a process for making an absorbent product by wet creping (fabric creping) from a cylinder prior to final drying. See U.S. Pat. Nos. 7,850,823; 7,585,388; 7,585,389; 7,662,257 and 7,399,378.

A "TAD Process" refers to through-air dried processes for making absorbent products. Throughdried, creped products are disclosed in the following patents: U.S. Pat. No. 3,994,771 to Morgan, Jr. et al.; U.S. Pat. No. 4,102,737 to Morton; and U.S. Pat. No. 4,529,480 to Trokhan. The processes described in these patents comprise, very generally, forming a web on a foraminous support, thermally pre-drying the web, applying the web to a Yankee dryer with a nip defined, in part, by an impression fabric, and creping the product from the Yankee dryer.

The absorbent characteristics of a product can be affected by the furnish, basis weight, strength, papermaking technology, and so forth. The sheet absorbency and converting technology for a specific product will impact the selection of bonding agent characteristics. CWP sheets are more consolidated than TAD sheets and therefore may have a lower wicking rate. Towel sheets commonly contain more softwood than tissue sheets, which may impact the pore size distribution of the web. It can be appreciated that an optimal bonding agent formula for one product may not be optimal for another.

Dry tensile strengths (MD or CD, which are the same for handsheets), stretch, ratios thereof, break modulus, stress and strain and other tensile characteristics are measured with a standard Instron test device or other suitable elongation tensile tester which may be configured in various ways, typically using 3 or 1 inch wide strips of tissue or towel, conditioned at 50% relative humidity and 23° C. (73.4° F.), with the tensile test run at a crosshead speed of 2 in/min for modulus, 10 in/min for tensile. Wet tensile is measured by the Finch cup method or following generally the procedure for dry tensile, wet tensile is measured by first drying the specimens at 100° C. or so and then applying a 1½ inch band of water across the width of the sample with a Payne Sponge Device prior to tensile measurement. The latter method is referred to as the sponge method. The Finch cup method uses a three-inch wide strip of tissue that is folded into a loop, clamped in the Finch Cup, then immersed in water. The Finch Cup, which is available from the Thwing-Albert Instrument Company of Philadelphia, Pa., is mounted onto a tensile tester equipped with a 2.0 pound load cell with the flange of the Finch Cup clamped by the tester's lower jaw and the ends of tissue loop clamped into the upper jaw of the tensile tester. The sample is immersed in water that has been adjusted to a pH of 7.0±0.1 and the tensile is tested after a 5 second immersion time. Tensile strengths are commonly expressed in units force per unit of width or simply in breaking length (BL) which is the tensile strength divided by the basis weight.

Wet/dry tensile ratios are simply ratios of the values determined by way of the foregoing methods. To express the ratio as a percent, it is multiplied by 100.

Tensile reduction is calculated relative to a control sample without debonder for purposes of comparison, i.e.: (Sample BL-[Control Sample w/o debonder BL]/[Control Sample w/o debonder BL])×100%.

A towel product is typically characterized by having predominantly (more than 50% by weight based on fiber content) softwood fiber.

A tissue product is typically characterized by having predominantly (more than 50% by weight based on fiber content) hardwood fiber.

Surfactants and Debonder/Softener Compositions

Zwitterionic surfactants of the invention have both cationic and anionic centers attached to the same molecule. The cationic part is based on imidazolinium (i.e., ammonium type) cations. The anionic part can be more variable and include sulfonates, carboxylates, phosphates and the like. Surfactants of the invention have the formula I:

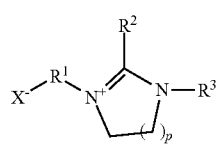

(I)

wherein:

$R^1$ is a straight or branched hydrocarbon spacer moiety having from 2-18 carbon atoms wherein said $R^1$ may be unsubstituted or optionally substituted with one or more groups which can be the same or different and are independently selected from the group consisting of halogen, cyano, alkyl, cycloalkyl, —OH, O($C_1$-$C_6$) alkyl, —$CO_2H$, —C(=O)O($C_1$-$C_6$) alkyl, N[($C_1$-$C_6$) alkyl]$_2$, and —NH[($C_1$-$C_6$) alkyl] and/or may have interposed within said hydrocarbon spacer moiety one or more groups which may be the same or different and are independently selected from the group consisting of —NH—C(O)—, —C(O)—NH—, —O—, —$SO_2$— and —C(=O)—;

$R^2$ is a straight or branched saturated or unsaturated hydrocarbon moiety having from 3 to 30 carbon atoms wherein said $R^2$:
  (i) may be unsubstituted or optionally substituted with one or more groups which can be the same or different and are independently selected from the group consisting of halogen, cyano, alkyl, cycloalkyl, —OH, O($C_1$-$C_6$) alkyl, —$CO_2H$, —C(=O)($C_1$-$C_6$) alkyl, —C(=O)O ($C_1$-$C_6$) alkyl, —N[($C_1$-$C_6$) alkyl]$_2$, —NH—C(O)($C_1$-$C_6$) alkyl, —C(O)NH$_2$, —C(O)—NH($C_1$-$C_6$) alkyl, and —NH($C_1$-$C_6$) alkyl, and/or
  (ii) may have interposed within said hydrocarbon moiety one or more groups which may be the same or different and are independently selected from the group consisting of —NH—C(O)—, —C(O)—NH—, —O—, —$SO_2$— and —C(=O)—;

$R^3$ is a straight or branched saturated or unsaturated hydrocarbon moiety having from 3 to 30 carbon atoms wherein said $R^3$:
  (i) may be unsubstituted or optionally substituted with one or more groups which can be the same or different and are independently selected from the group consisting of halogen, cyano, alkyl, cycloalkyl, —OH, O($C_1$-$C_6$) alkyl, —$CO_2H$, —C(=O)($C_1$-$C_6$) alkyl, —C(=O)O ($C_1$-$C_6$) alkyl, —N[($C_1$-$C_6$) alkyl]$_2$, —NH—C(O)($C_1$-$C_6$) alkyl, —C(O)NH$_2$, —C(O)—NH($C_1$-$C_6$) alkyl, and —NH($C_1$-$C_6$) alkyl, and/or
  (ii) may have interposed within said hydrocarbon moiety one or more groups which may be the same or different and are independently selected from the group consisting of —NH—C(O)—, —C(O)—NH—, —O—, —$SO_2$— and —C(=O)—;

wherein at least one of $R^2$ or $R^3$ or has from 8 to 30 carbon atoms;

X is selected from the group consisting of $SO_3$, $CO_2$, $PO_3$ and $HPO_2$; and p is 1 or 2.

The surfactants of the invention may be used along with conventional debonder and/or softener components, including conventional cationic surfactants if so desired. There is disclosed in U.S. Pat. No. 7,736,464 to Kokko a debonder composition including a combination of: (a) a quaternary ammonium surfactant component; and (b) a nonionic surfactant component, any of which may be used with the invention zwitterionic surfactants. The surfactants of the invention are most preferably used in debonder compositions along with a nonionic surfactant, for example those selected from the group consisting of alkoxylated fatty acids and alkoxylated fatty alcohols. Typically the nonionic surfactant includes the reaction product of a fatty acid or fatty alcohol with ethylene oxide such as a polyethylene glycol diester of a fatty acid (PEG mono or diols or PEG mono or diesters). One preferred composition which is used in connection with the present invention includes 15 wt % of imidazolinium zwitterion surfactants in a 1:1 mixture of PEG-400-mono and dioleates.

Other conventional debonder/softener components which may be used are disclosed in the following references: U.S. Pat. No. 5,622,597 to Callen et al.; U.S. Pat. No. 4,441,962 to Osborn, III and U.S. Pat. No. 4,351,699 also to Osborn, III; U.S. Pat. No. 5,698,076 to Phan et al.; U.S. Pat. No. 5,730,839 to Wendt et al.; U.S. Pat. No. 5,753,079 to Jenny et al.; U.S. Pat. No. 4,447,294 to Osborn, III; U.S. Pat. No. 5,279,767 to Phan et al. and U.S. Pat. No. 5,240,562 of Phan et al.

Debonder and or softener compositions may be applied to the sheet by any suitable method such as spraying or more typically by way of adding the debonder to the aqueous furnish in the headbox of a papermaking machine used to produce the sheet. In cases where a multilayer headbox is used to produce plies having multiple layers, treatment levels of debonder apply to any layer provided to the sheet. For example, if one layer has no added debonder (other than perhaps residual debonder in the water provided to the furnish) and another layer is treated at 4 lbs debonder/ton of papermaking fiber in the sheet, then the basesheet furnish is considered to be treated at a level of 4 lbs debonder/ton.

Charge density of the debonder composition is determined by any suitable technique. One procedure generally is seen in U.S. Pat. No. 8,852,399 to Neal et al., Cols. 51-52. Charge density is preferably measured using a Mutek titrator, or equivalent instrument. The charge density (charge demand) of the debonder composition herein is reported in meq/g units, determined as follows:

A Mutek PCD 05 Travel streaming current detector with titrator, deionized water, a top pan balance (capacity>400 gm), an auto pipetter with disposable tips or transfer pipettes, 250 ml beakers are used with the following reagents:

PVSK Solution: Potassium salt of polyvinyl sulfate, 0.001 N, (BTG Americas Customer Support, 5085 Avalon Ridge PKWY, Norcross, Ga. 30071) or DADMAC Solution: Di-Allyl di-methyl ammonium chloride, 0.001 N, BTG Americas Customer Support, 5085 Avalon Ridge PKWY, Norcross, Ga. 30071). The procedure employed is:

1. Determine the solids content of the polymer that is to be analyzed for charge density, (% solids A.R).

2. Weigh approximately 0.20-0.75 gm of the polymer (record the actual weight as gm. A.R.) into a 250 ml beaker, dilute with deionized water to make a 100 gm "stock solution". Mix thoroughly.

3. Weigh 5.00 gm. of the stock solution into another 250 ml beaker and dilute to 100 gm with deionized water and mix well. This is your "working solution".

4. Weigh 10.00 gm of the working solution into the Mutek sample cup and turn on the Mutek. Wait 1-2 minutes until the streaming current potential has stabilized before starting the titration. (This is essential to get an accurate titration value.)

5. After noting the sign (+ or −) of the mV reading from the digital read out of the Mutek PCD, insert the appropriate burette tip (DADMAC for negatively charged solutions or PVSK for positively charged solutions) into the Mutek burette holder. Position the burette tip so that it touches the back inner wall of the sample cup. Do not immerse the tip in the sample.

6. Start the titration. When the titration has reached the endpoint the titrator will display the volume of titrant required to reach a "0 mV" reading. Record this titer value.

Sample Calculation

Charge Density (meq/gm) =

$$\frac{(\text{ml titer})(0.001 \text{ meq/ml})}{(10 \text{ gm working sol.})(\text{gm } A.R./100 \text{ gm})}$$
$$(\% \text{ solids } A.R./100 \text{ gm})(5 \text{ gm stock sol.}/100 \text{ gm})$$

Synthesis Examples 1. 4-(2-((Z)-heptadec-8-en-1-yl)-1-(2-oleamidoethyl)-4,5-dihydro-1H-imidazol-3-ium-3-yl)butane-1-sulfonate, Compound 1 (z-IM-3):

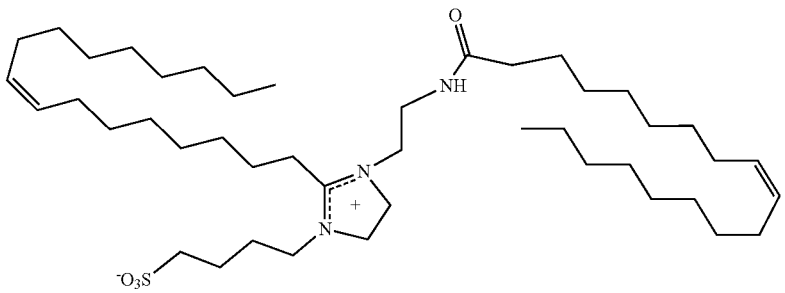

A reactor was charged with 54.89 g (0.186 mol) methyl-oleate, 9.55 g (0.093 mol) diethylenetriamine and heated under an argon atmosphere with stirring to 160° C., whereupon methanol began to reflux, enough methanol was distilled off to bring to 180° C., stirring with argon sparging was continued for 2 days to yield pure 3-(2-((z)-hepatadec-8-en-1-yl)-1-(2-oleamido ethyl)-4,5-dihydro-1H-imidazoline (Im) as a viscous light straw colored fluid. $^{13}$C NMR (CDCl$_3$, 100 MHz) δ=25.8, 36.6, 38.0, 46.6, 50.2, 52.2, 167.5, 173.4. A flask was charged with 6.14 g (0.01 mol) 3-(2-((z)-hepatadec-8-en-1-yl)-1-(2-oleamido ethyl)-4,5-dihydro-1H-imidazoline, 1.36 g (0.01 mol) 1,4-butane sultone, and 20 ml anhydrous N-Methyl-2-pyrrolidone (NMP), heated under an argon atmosphere with stirring at 140° C. for 2 days. Evaporated the mixture in vacuo (90° C./0.8 mmHg). A viscous dark amber wax like solid comprised of more than 90 wt % of 4-(2-((Z)-heptadec-8-en-1-yl)-1-(2-oleamidoethyl)-4,5-dihydro-1H-imidazol-3-ium-3-yl)bu-tane-1-sulfonate (z-Im-3) was obtained. $^{13}$C NMR (CDCl$_3$, 100 MHz), δ=25.6, 36.0, 36.4, 46.5, 47.0, 47.4, 47.6, 50.1, 168.5, 174.8. The compound was obtained at high yield (>90%). This compound formed stable debonder compositions with nonionic surfactants such as PEG oleates.

2. 3-(2-((Z)-heptadec-8-en-1-yl)-1-(2-oleamidoethyl)-4,5-dihydro-1H-imidazol-3-ium-3-yl)propane-1-sulfonate, Compound 2 (z-Im-2):

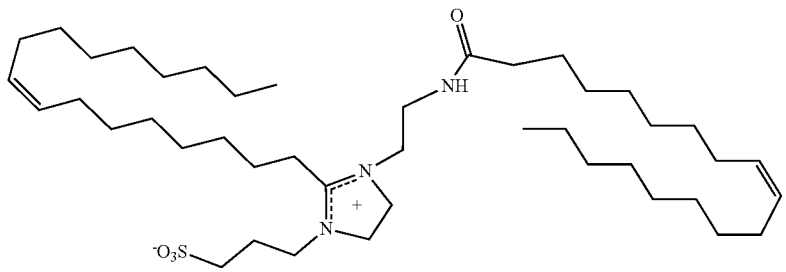

was prepared following the procedure of Example 1, substituting 1,3-propane sultone for butane sultone. The compound was obtained at high yield (>90%). This compound formed stable debonder compositions with nonionic surfactants such as PEG oleates.

3. 2-(2-((Z)-heptadec-8-en-1-yl)-1-(2-oleamidoethyl)-4,5-dihydro-1H-imidazol-3-ium-3-yl)ethane-1-sulfonate, Compound 3 (z-IM-1):

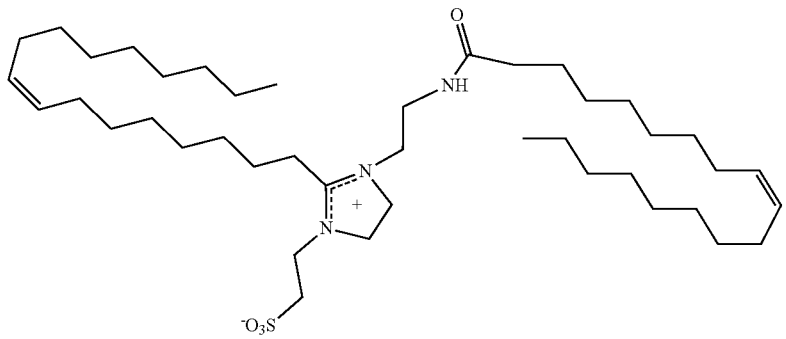

A reactor was charged with 54.89 g (0.186 mol) methyloleate, 9.55 g (0.093 mol) diethylenetriamine and heated under an argon atmosphere with stirring to 160° C., whereupon methanol began to reflux, enough methanol was distilled off to bring to 180° C., stirring with argon sparging was continued for 2 days to yield pure 3-(2-((z)-hepatadec-8-en-1-yl)-1-(2-oleamido ethyl)-4,5-dihydro-1H-imidazoline as a viscous light straw colored fluid. $^{13}$C NMR (ppm in CDCl$_3$, 100 MHz) δ=25.8, 36.6, 38.0, 46.6, 50.2, 52.2, 167.5, 173.4. A flask was charged with 4.000 g (6.514 mmol) 3-(2-((z)-hepatadec-8-en-1-yl)-1-(2-oleamido ethyl)-4,5-dihydro-1H-imidazoline, 1.648 g (7.810 mmol) sodium 2-bromoethylsulfonate, 20 ml anhydrous N-Methyl-2-pyrrolidone (NMP), heated under an argon atmosphere with stirring at 140° C. for 2 days. Evaporated the mixture in vacuo (90° C./0.8 mmHg), poured into 30 mL sodium chloride saturated deionized water, extracted with 20 mL aliquots of chloroform until the chloroform layer had only a faint color, combined the chloroform layer and dried over anhydrous magnesium sulfate, filtered through celite, vacuum distilled. A viscous dark amber fluid comprised of about 38 wt % of 2-(2-((Z)-heptadec-8-en-1-yl)-1-(2-oleamidoethyl)-4,5-dihydro-1H-imidazol-3-ium-3-yl)ethane-1-sulfonate (z-Im-1), 48 wt % Im and 15 wt % of NMP was obtained. The product was purified using flash chromatography with MeOH-water (9:1), and yield 80 mol % of z-IM-1. $^{13}$C NMR (ppm in CDCl$_3$, 100 MHz) δ=170.8, 46.7, 47.4, 36.0, 46.3, 174.8, 25.7, 43.4, 45.7, 362, 25.6.

Debonder Testing

Debonders were formulated with Compound 1 (z-IM-3) and Compound 2 (z-IM-2) by admixing 15 wt. % of these surfactants into PEG-400 monooleate. The debonder composition formulated with Compound 1 is identified herein and in the appended Figures as DBC1, while the debonder composition formulated with Compound 2 is referred to herein and in the appended Figures as DBC2. A Control debonder, CDB, was formulated with 15 wt. % of the corresponding imidazolinium salt, this control surfactant having the same structure except for the alkyl sulfonate substitution. DBC1 has a charge density of −0.05 meq/g while the control bebonder composition has a positive charge density which is considerably higher.

Handsheet experiments were designed to determine the performance of zwitterionic-type debonders when dosed with permanent wet strength resin (pWSR) or temporary wet strength resin (tWSR) as follows: 1. debonder added with PAE type pWSR (Amres® 1100E) and 2. debonder added with cationic type tWSR (Kemira Fennorez® 110). The debonder formulations DBC1, DBC2 and the Control CDB were directly compared in handsheets over a dosage range of 0-8 lb as-received formulation/T. Freshly prepared 1 wt % water solutions of a given dosage of DBC1, DBC2 and the Control CDB were used for this study.

In a first series of experiments a given 10.00 g (oven dry weight) sample of an unrefined 65:35 mixture of softwood and hardwood furnish was suspended in 300 mL of tap water, a given dosage of DBC1, DBC2 or Control CDB was added after given dosage of Amres® 1100E (10 #/T) and stirred 5 min, tested for titratable charge by titration with either a 0.001 N solution of poly(diallyldimethylammonium chloride) (PDADMAC) or poly(vinylsulfate potassium) (PVSK) using a Mutek PCD-03 instrument as detector. The salvageable components were recombined with the treated slurry, diluted to 600 mL and tested for zeta-potential with a Mutek SZP-10 zeta potential meter. The furnish was diluted to 8.0 L, formed into British handsheets, pressed at 15 psi for 5 min, and dried on rotating dryer drum at 250° F.

In a second series of experiments, a given 10.00 g (O.D. wt.) sample of an unrefined 65:35 mixture of softwood and hardwood furnish were suspended in 300 mL of tap water, a given dosage of DBC1, DBC2 or Control CDB was added before given dosage of Amres® 1100E (10 #/T) and stirred 5 min, tested for titratable charge by titration with either a 0.001 N solution of PDADMAC or PVSK using a Mutek PCD-03 instrument as detector. The salvageable components were recombined with the treated slurry, diluted to 600 mL and tested for zeta-potential with a Mutek SZP-10 zeta potential meter. The furnish was diluted to 8.0 L, formed into British handsheets, pressed at 15 psi for 5 min, and dried on rotating dryer drum at 250° F.

In a third series of experiments, a given 10.00 g (O.D. wt.) sample of an unrefined 35:65 mixture of softwood and hardwood furnish were suspended in 300 mL of tap water, a given dosage of DBC1, DBC2 or Control CDB was added after given dosage of Kemira Fennorez 110 (7 #/T) and stirred 5 min, tested for titratable charge by titration with either a 0.001 N solution of PDADMAC or PVSK using a Mutek PCD-03 instrument as detector. The salvageable components were recombined with the treated slurry, diluted to 600 mL and tested for zeta-potential with a Mutek SZP-10 zeta potential meter. The furnish was diluted to 8.0 L, formed into British handsheets, pressed at 15 psi for 5 min, and dried on rotating dryer drum at 250° F.

Results, including titratable charge and zeta potential of the furnish, as well as tensile properties of the handsheets, appear in Tables 1-3 and are summarized in the discussion which follows and the attached Figures.

A. Debonder Addition after Amres® 1100E

In Table 1, Sample 1 is the reference which was dosed only by Amres® 1110E (10 #/T), both titratable charge and zeta potential were positive, which implies the fibers had become cationic after Amres® 1100E (10 #/T) dosing. When the pulp slurry was dosed with Amres® 1110E (10 #/T) prior to the zwitterion debonder dose, the titratable charge of the zwitterion debonder cells remained the same (slightly negative) as the dose was increased, while the titratable charge of Control CDB cell kept positive and increasing. The zeta potentials decreased as the zwitterion debonder doses increased. This implies that anionic zwitterion debonder was being retained on the fibers. Table 1 shows the titratable charges, zeta-potentials and handsheet properties.

Tensile reduction is calculated relative to Sample 1 (no debonder) in each of the three trials: (Sample BL-Sample 1 BL/Sample 1 BL)×100%.

TABLE 1

Debonder added after Amres ® 1100E.

| Sample ID | Debonder | Dose (#/T) | Titratable Charge (ml/ 10 ml) | Zeta Potential (mV) | Basis Weight (gm/m$^2$) | Dry Breaking Length (Km) | Wet Breaking Length (Km) | W/D |
|---|---|---|---|---|---|---|---|---|
| 1 |  | 0 | 0.03 | 44 | 52.74 | 2.13 | 0.54 | 0.25 |
| 2 | DBC2 | 2 | −0.03 | 34 | 54.14 | 1.90 | 0.49 | 0.26 |
| 3 |  | 4 | −0.03 | 29 | 53.72 | 1.63 | 0.43 | 0.26 |
| 4 |  | 6 | −0.03 | 27 | 53.51 | 1.39 | 0.38 | 0.27 |
| 5 |  | 8 | −0.04 | 23 | 54.66 | 1.22 | 0.34 | 0.28 |
| 7 | DBC1 | 2 | −0.02 | 33 | 52.84 | 1.88 | 0.48 | 0.26 |
| 8 |  | 4 | −0.04 | 29 | 53.93 | 1.56 | 0.44 | 0.28 |
| 9 |  | 6 | −0.03 | 26 | 53.64 | 1.39 | 0.37 | 0.27 |
| 10 |  | 8 | −0.04 | 23 | 53.68 | 1.14 | 0.32 | 0.28 |
| 12 | CDB | 2 | 0.06 | 46 | 53.82 | 2.00 | 0.51 | 0.26 |
| 13 |  | 4 | 0.07 | 45 | 54.60 | 1.79 | 0.44 | 0.25 |
| 14 |  | 6 | 0.08 | 46 | 54.71 | 1.51 | 0.41 | 0.27 |
| 15 |  | 8 | 0.11 | 48 | 54.12 | 1.46 | 0.37 | 0.25 |

Figure 1B:
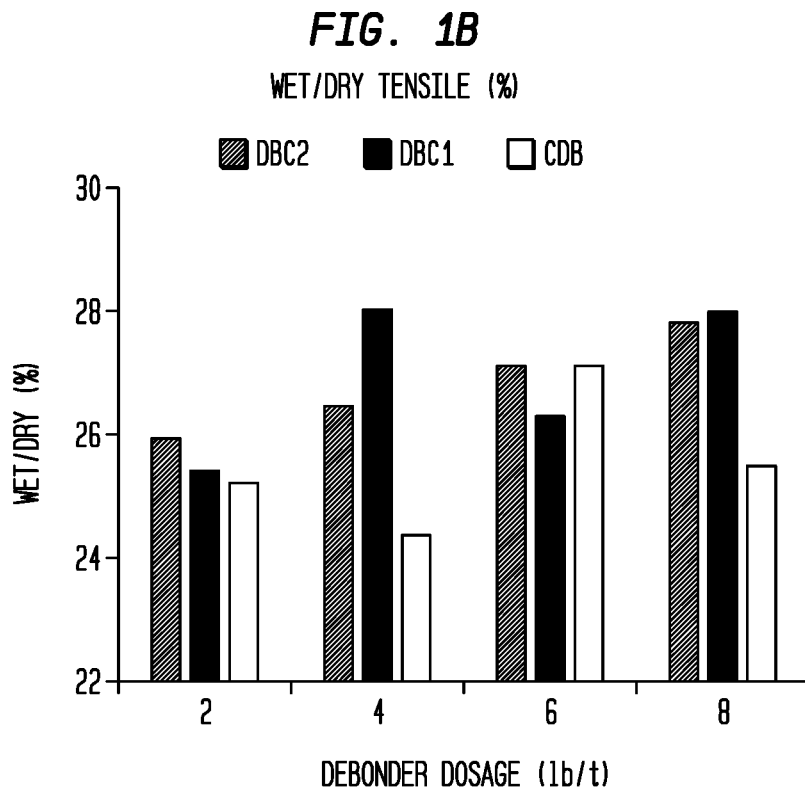
FIG. 1B is a histogram of wet/dry tensile ratios for handsheets, wherein the furnish was treated with cationic permanent wet strength resin prior to adding debonder.

Furnish = HW/SW dry lap (35/65)
All samples dosed with 10 #/T Ames ® 1110E prior to debonder addition FIGS. 1A and 1B show the tensile reduction and wet/dry tensile vs. debonder dosage. Both zwitterion debonder formulations DBC1 and DBC2 showed improved tensile reduction compared to the Control debonder over the whole dosage range, which implies zwitterion debonders had a better retention rate compared to the Control cationic debonder if we dosed Amres® 1100E prior to debonder. Zwitterion debonders showed an anionic property believed to be due to the strongly acidic nature of sulfonic acid (the conjugate acid of the sulfonate moiety present in the zwitterion), and interacted better with the fibers which became cationic after Amres® 1100E dosed. The cationic Control debonder competed with cationic WSR on the fiber, lowered its retention rate and impaired debond performance. Zwitterion debonders also showed similar or better W/D compared to the Control debonder.

B. Debonder Addition Before Amres® 1100E

When the pulp slurry was dosed with Amres® 1110E (10 #/T) after the zwitterion debonder dose, the titratable charge of the zwitterion debonder cells decreased as the dose was increased, while the titratable charge of the Control debonder cell kept increasing. The zeta potentials in the zwitterion debonder cells decreased as the zwitterion debonder doses increased, while the zeta potential of the Control debonder cell increases as debonder dosage increased; as shown in Table 2.

TABLE 2

Debonder added before Amres ® 1100.

| Sample ID | Debonder | Dose (#/T) | Titratable Charge (ml/ 10 ml) | Zeta Potential (mV) | Basis Weight (gm/m$^2$) | Dry Breaking Length (Km) | Wet Breaking Length (Km) | W/D |
|---|---|---|---|---|---|---|---|---|
| 1 |  | 0 | 0.08 | 45 | 53.69 | 2.07 | 0.51 | 0.25 |
| 2 | DBC2 | 2 | 0.15 | 41 | 53.19 | 1.94 | 0.51 | 0.26 |
| 3 |  | 4 | 0.09 | 40 | 52.81 | 1.58 | 0.45 | 0.28 |
| 4 |  | 6 | 0.08 | 37 | 53.31 | 1.20 | 0.37 | 0.31 |
| 5 |  | 8 | 0.06 | 35 | 53.84 | 1.16 | 0.32 | 0.28 |
| 7 | DBC1 | 2 | 0.15 | 40 | 53.13 | 1.73 | 0.46 | 0.27 |
| 8 |  | 4 | 0.08 | 37 | 54.09 | 1.36 | 0.4 | 0.29 |
| 9 |  | 6 | 0.06 | 35 | 53.36 | 1.30 | 0.39 | 0.30 |
| 10 |  | 8 | 0.07 | 39 | 53.16 | 1.10 | 0.35 | 0.32 |
| 12 | CDB | 2 | 0.09 | 49 | 53.11 | 1.72 | 0.47 | 0.27 |
| 13 |  | 4 | 0.08 | 49 | 53.4 | 1.39 | 0.43 | 0.31 |
| 14 |  | 6 | 0.11 | 50 | 53.94 | 1.41 | 0.39 | 0.28 |
| 15 |  | 8 | 0.15 | 51 | 54.6 | 1.17 | 0.34 | 0.29 |

Figure 2A:
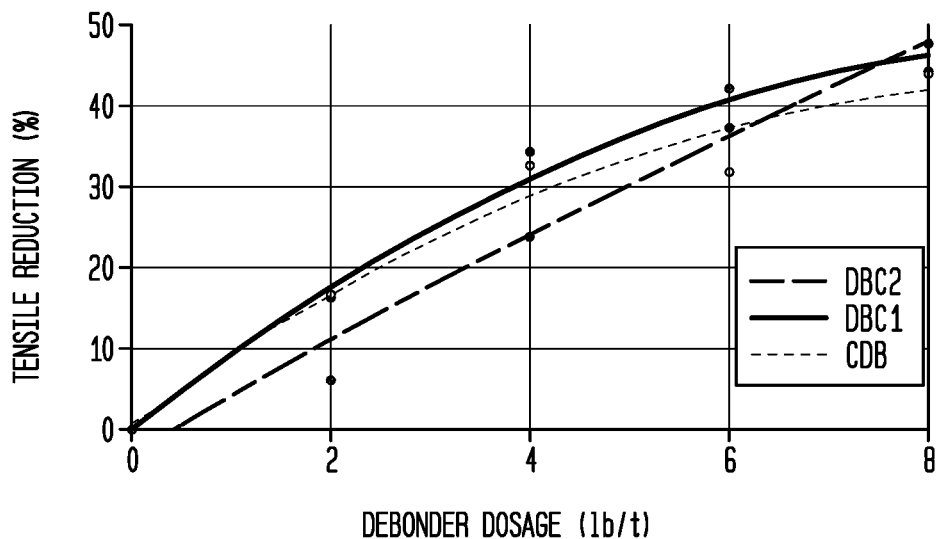
FIG. 2A is a plot of tensile reduction versus debonder dosage for handsheets, wherein the furnish was treated with cationic permanent wet strength resin after adding debonder.
Figure 2B:
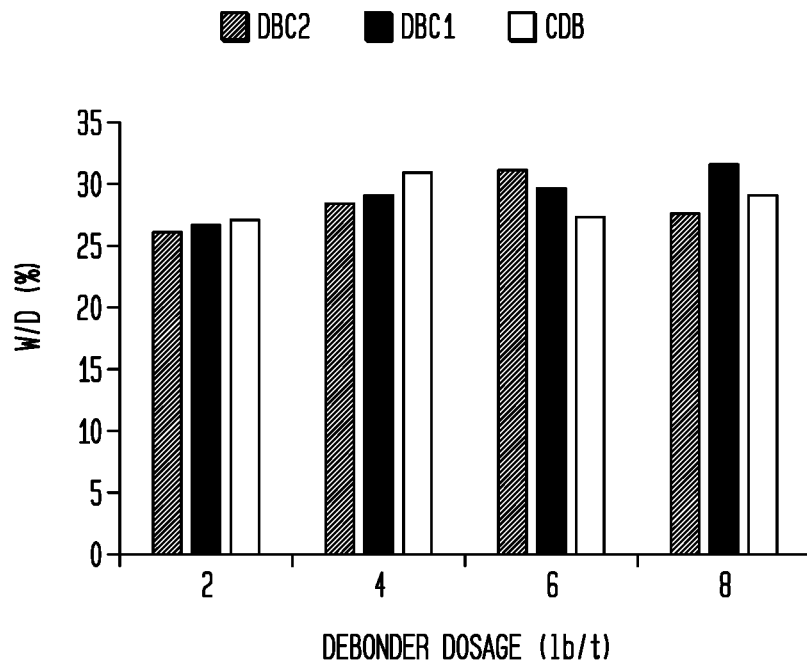
FIG. 2B is a histogram of wet/dry tensile ratios for handsheets, wherein the furnish was treated with cationic permanent wet strength resin after adding debonder.

Furnish = HW/SW dry lap (35/65)
All samples dosed with 10 #/t Amres ® 1110E after debonder addition FIGS. 2A and 2B show the tensile reduction and wet/dry tensile vs. debonder dosage. DBC1 showed similar tensile reduction at lower dosage compared to the Control debonder, but outperformed the Control debonder at higher dosage. DBC2 didn't perform as well as the Control debonder at low dosage, but became better at higher dosage. Wet/Dry tensile didn't show significant difference between zwitterion debonders and Control debonder cells.

Figure 3:
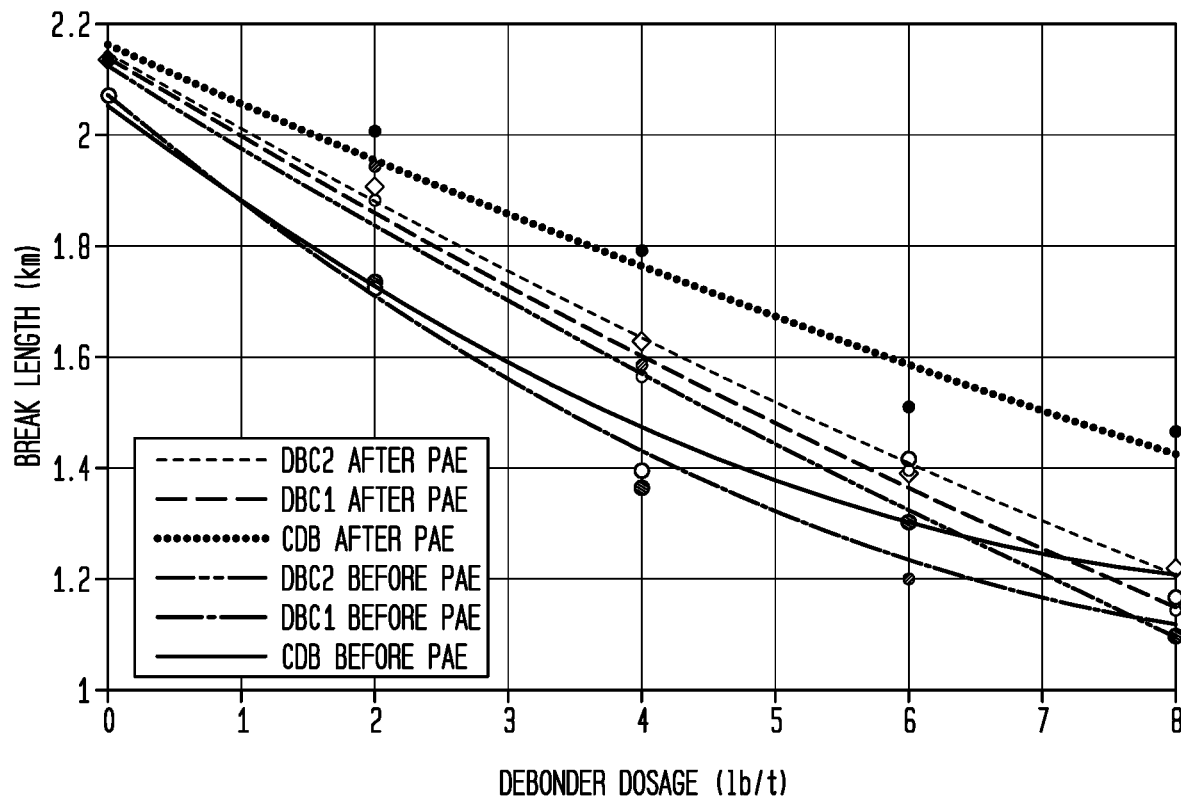
FIG. 3 is a plot of dry breaking length versus debonder dosage for various products.

It is important to consider the adding sequence of pWSR and debonders. If pWSR were added prior to debonder, the anionic fiber would be saturated by cationic pWSR and built higher dry strength compared to adding pWSR after debonder at the same pWSR dosage. In FIG. 3, the Control debonder after PAE showed highest dry strength over the whole dosage range due to the pre-built strength by adding WSR first and lower retention rate of cationic debonder. Both DBC1 and DBC2 showed better debond performance than the Control debonder when they were all added after WSR, which indicates DBC2 and DBC1 controlled the stock charge better and was retained more in the handsheets. When debonders were added prior to WSR, DBC1 debonded better than the Control debonder and DBC2. The wet/dry tensile of zwitterion debonder dosed handsheets showed no significant difference compared to those dosed with the Control cationic debonder.

To improve the strength of handsheets, WSR should be added first, then add debonder to provide some softness. In this case, zwitterion debonder debonded better than the Control cationic debonder. Adding debonder first could improve the debond performance. Cationic debonder would consume the anionic sites on the fiber first, which may lower the retention rate of WSR and therefor decrease the tensile of the handsheets.

C. Debonders Addition after Kemira Fennorez® 110

In this series of experiments, debonders were dosed after temporary wet strength resin Fennorez® 110 (7 #/T), a glyoxylated polyacrylamide type tWSR. The titratable charge of the zwitterion debonder cells remained the same or slightly negative as the dose was increased, while the titratable charge of the Control debonder cell kept increasing and was positive at most testing points. The zeta potentials decreased as the zwitterion debonder doses increased as well. Here again, this implies that the debonder was being retained on the fibers, as shown in Table 3. In most cases, DBC1 debonded better than DBC2 and the Control debonder, CDB.

TABLE 3

Debonder added after Fennorez ® 110.

| Sample ID | Debonder | Dose (#/T) | Titratable Charge (ml/ 10 ml) | Zeta Potential (mV) | Basis Weight (gm/m$^2$) | Dry Breaking Length (Km) |
|---|---|---|---|---|---|---|
| 1 |  | 0 | −0.07 | 32 | 52.66 | 2.34 |
| 2 | DBC2 | 2 | −0.06 | 22 | 53.28 | 2.05 |
| 3 |  | 4 | −0.06 | 17 | 52.52 | 1.73 |
| 4 |  | 6 | −0.06 | 13 | 53.34 | 1.56 |
| 5 |  | 8 | −0.04 | 11 | 52.81 | 1.42 |
| 6 | DBC1 | 2 | −0.07 | 20 | 52.88 | 1.93 |
| 7 |  | 4 | −0.05 | 14 | 53.36 | 1.77 |
| 8 |  | 6 | −0.07 | 11 | 53.88 | 1.33 |
| 9 |  | 8 | −0.07 | 9 | 54.19 | 1.42 |
| 10 | CDB | 2 | −0.01 | 34 | 53.20 | 1.71 |
| 11 |  | 4 | 0.07 | 36 | 52.70 | 1.86 |
| 12 |  | 6 | 0.10 | 40 | 53.08 | 1.42 |
| 13 |  | 8 | 0.13 | 39 | 53.40 | 1.49 |

Figure 4:
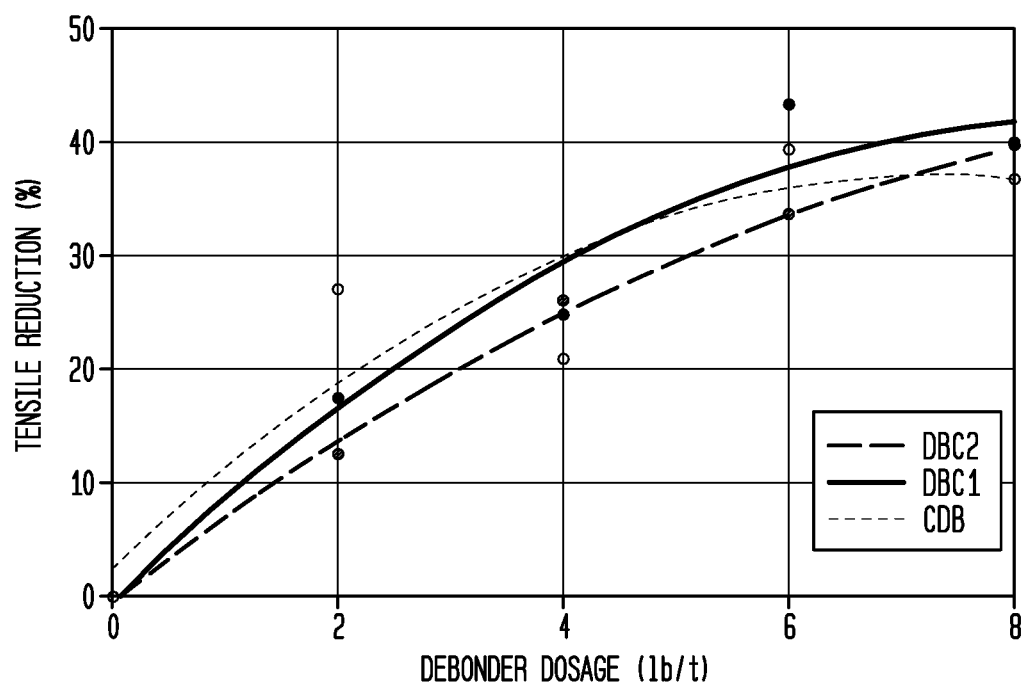
FIG. 4 is a plot of tensile reduction versus debonder dosage for handsheets, wherein the furnish was treated with cationic temporary wet strength resin prior to adding debonder.

Furnish = HW/SW dry lap (65/35)
All samples dosed with 7 #/T Kemira Fennorez ® 110 prior to debonder addition When dosed with tWSR, zwitterion debonder exhibited a similar tensile reduction as the cationic Control debonder, CDB as shown in FIG. 4.

It should be noted that: 1. Kemira Fennorez® 110 is a tWSR with relatively high cationic charge density; and 2. although debonder and tWSR were dosed together in trials, it is unusual in practice to dose debonder and tWSR at the same layer in connection with commercial manufacture. More commonly in commercial practice, when tWSR and debonder are used in an absorbent product a layered headbox is used and tWSR is added to that portion of the furnish making up the bottom layer of the product and debonder is added to that portion of the furnish making up the top layer of the product.

pWSR and debonder may be dosed together in the same layer for towel products when using a multilayer headbox.

Zwitterion debonder formulations tested did not debond handsheets when they were dosed by themselves due possibly to the stronger anionic properties of sulfonate type zwitterion debonders. However, when they were dosed with permanent wet strength resin (pWSR), DBC1 and DBC2 exhibited similar or better debond performance and better charge control compared to the Control CDB. Addition points of the debonders can greatly influence the tensile reduction of the handsheets; hence adding debonders prior to pWSR debonded better than adding after pWSR. When zwitterion debonders were dosed with temporary wet strength resin (tWSR), DBC1 outperformed DBC2 and CDB debonder in tensile reduction. DBC1 debonder exhibited best debond performance and charge control in both tissue and towel type handsheet production.

D. Structured Basesheet Trials

A Structured Basesheet Process was used to made absorbent sheet product by wet creping (fabric creping) from a cylinder prior to final drying. The apparatus employed was of the class described in U.S. Pat. No. 7,399,378 as is shown in FIG. 5.

Figure 5:
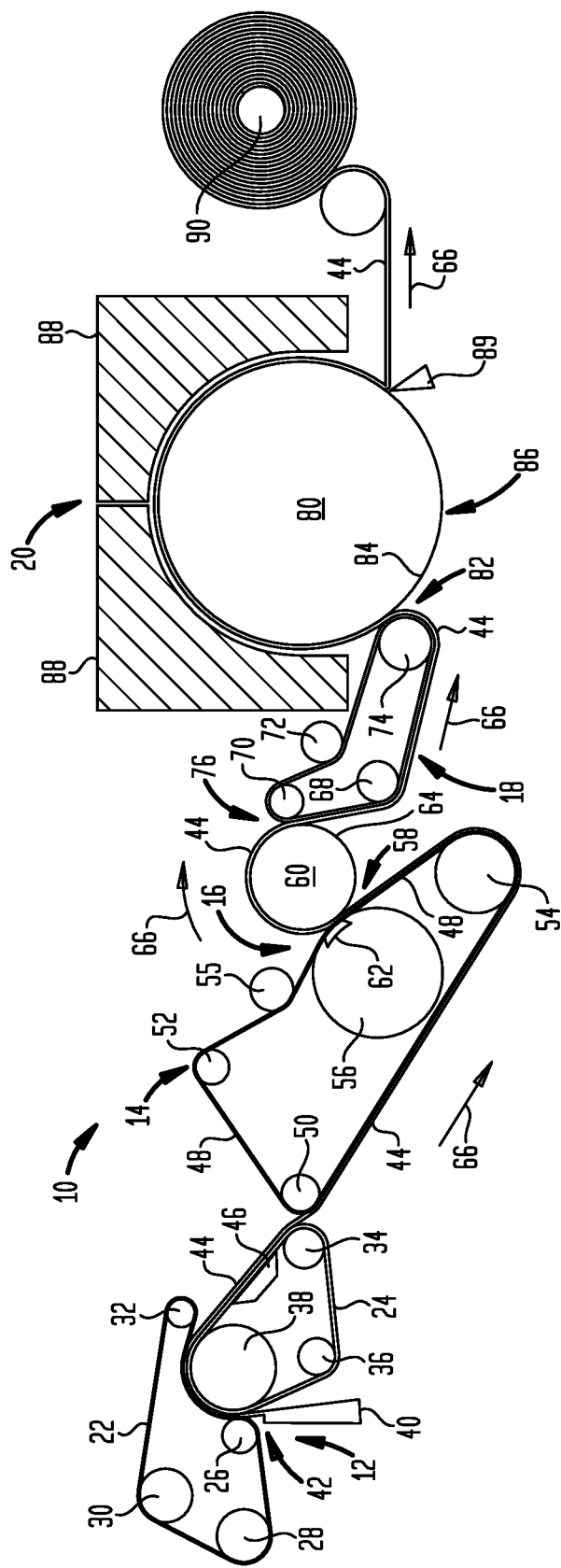
FIG. 5 is a schematic diagram of an apparatus for making structured basesheet.

FIG. 5 is a schematic diagram of a papermachine 10 having a conventional twin wire forming section 12, a felt run 14, a shoe press section 16, a creping fabric 18 and a Yankee dryer 20 suitable for practicing the present invention. Forming section 12 includes a pair of forming fabrics 22, 24 supported by a plurality of rolls 26, 28, 30, 32, 34, 36 and a forming roll 38. A headbox 40 provides papermaking furnish to a nip 42 between forming roll 38 and roll 26 and the fabrics. The furnish forms a nascent web 44 which is dewatered on the fabrics with the assistance of vacuum, for example, by way of vacuum box 46.

The nascent web is advanced to a papermaking felt 48 which is supported by a plurality of rolls 50, 52, 54, 55 and the felt is in contact with a shoe press roll 56. The web is of low consistency as it is transferred to the felt. Transfer may be assisted by vacuum; for example roll 50 may be a vacuum roll if so desired or a pickup or vacuum shoe as is known in the art. As the web reaches the shoe press roll it may have a consistency of 10-25 percent, preferably 20 to 25 percent or so as it enters nip 58 between shoe press roll 56 and transfer roll 60. Transfer roll 60 may be a heated roll if so desired. Instead of a shoe press roll, roll 56 could be a conventional suction pressure roll. If a shoe press is employed it is desirable and preferred that roll 54 is a vacuum roll effective to remove water from the felt prior to the felt entering the shoe press nip since water from the furnish will be pressed into the felt in the shoe press nip. In any case, using a vacuum roll at 54 is typically desirable to ensure the web remains in contact with the felt during the direction change as one of skill in the art will appreciate from the diagram.

Web 44 is wet-pressed on the felt in nip 58 with the assistance of pressure shoe 62. The web is thus compactively dewatered at 58, typically by increasing the consistency by 15 or more points at this stage of the process. The configuration shown at 58 is generally termed a shoe press. Cylinder 60 is operative as a transfer cylinder which operates to convey web 44 at high speed, typically 1000 fpm-6000 fpm to the creping fabric.

Cylinder 60 has a smooth surface 64 which may be provided with adhesive and/or release agents if needed. Web 44 is adhered to transfer surface 64 of cylinder 60 which is rotating at a high angular velocity as the web continues to advance in the machine-direction indicated by arrows 66. On the cylinder, web 44 has a generally random apparent distribution of fiber.

Direction 66 is referred to as the machine-direction (MD) of the web as well as that of papermachine 10; whereas the cross-machine-direction (CD) is the direction in the plane of the web perpendicular to the MD.

Web 44 enters nip 58 typically at consistencies of 10-25 percent or so and is dewatered and dried to consistencies of from about 25 to about 70 by the time it is transferred to creping fabric 18 as shown in the diagram.

Fabric 18 is supported on a plurality of rolls 68, 70, 72 and a press nip roll 74 and forms a fabric crepe nip 76 with transfer cylinder 60 as shown.

The creping fabric defines a creping nip over the distance in which creping fabric 18 is adapted to contact roll 60; that is, applies significant pressure to the web against the transfer cylinder. To this end, backing (or creping) roll 70 may be provided with a soft deformable surface which will increase the length of the creping nip and increase the fabric creping angle between the fabric and the sheet and the point of contact or a shoe press roll could be used as roll 70 to increase effective contact with the web in high impact fabric creping nip 76 where web 44 is transferred to fabric 18 and advanced in the machine-direction.

Creping nip 76 generally extends over a fabric creping nip distance of anywhere from about ⅛" to about 2", typically ½" to 2". For a creping fabric with 32 CD strands per inch, web 44 thus will encounter anywhere from about 4 to 64 weft filaments in the nip.

The nip pressure in nip 76, that is, the loading between backing roll 70 and transfer roll 60 is suitably 20-100, preferably 40-70 pounds per linear inch (PLI).

After fabric creping, the web continues to advance along MD 66 where it is wet-pressed onto Yankee cylinder 80 in transfer nip 82. Transfer at nip 82 occurs at a web consistency of generally from about 25 to about 70 percent. At these consistencies, it is difficult to adhere the web to surface 84 of cylinder 80 firmly enough to remove the web from the fabric thoroughly. This aspect of the process is important, particularly when it is desired to use a high velocity drying hood as well as maintain high impact creping conditions.

The web is dried on Yankee cylinder 80 which is a heated cylinder and by high jet velocity impingement air in Yankee hood 88. As the cylinder rotates, web 44 is creped from the cylinder by creping doctor 89 and wound on a take-up roll 90. Creping of the paper from a Yankee dryer may be carried out using an undulatory creping blade, such as that disclosed in U.S. Pat. No. 5,690,788, the disclosure of which is incorporated by reference. Use of the undulatory crepe blade has been shown to impart several advantages when used in production of tissue products. In general, tissue products creped using an undulatory blade have higher caliper (thickness), increased CD stretch, and a higher void volume than do comparable tissue products produced using conventional crepe blades. All of these changes effected by use of the undulatory blade tend to correlate with improved softness perception of the tissue products.

Utilizing an apparatus and process of the class described above, structured basesheet was prepared and tested to determine the synergistic effect of DBC2 with Amres® 1110E permanent wet strength resin and Amtex Gelycel CMC. A stratified headbox was used with a 35/65 Furnish Split where the Yankee layer was 100% SW and the air layer was 40% SW/60% HW. Amres® 1110E and Amtex Gelycel CMC were fixed at 12 lb/t of fiber and 4 lb/t of fiber respectively. DCB2 levels of 0, 5 and 10 lb/ton were employed. DBC2 was added to the paperstock first when used, followed by wet strength resin and then CMC.

Figure 6:
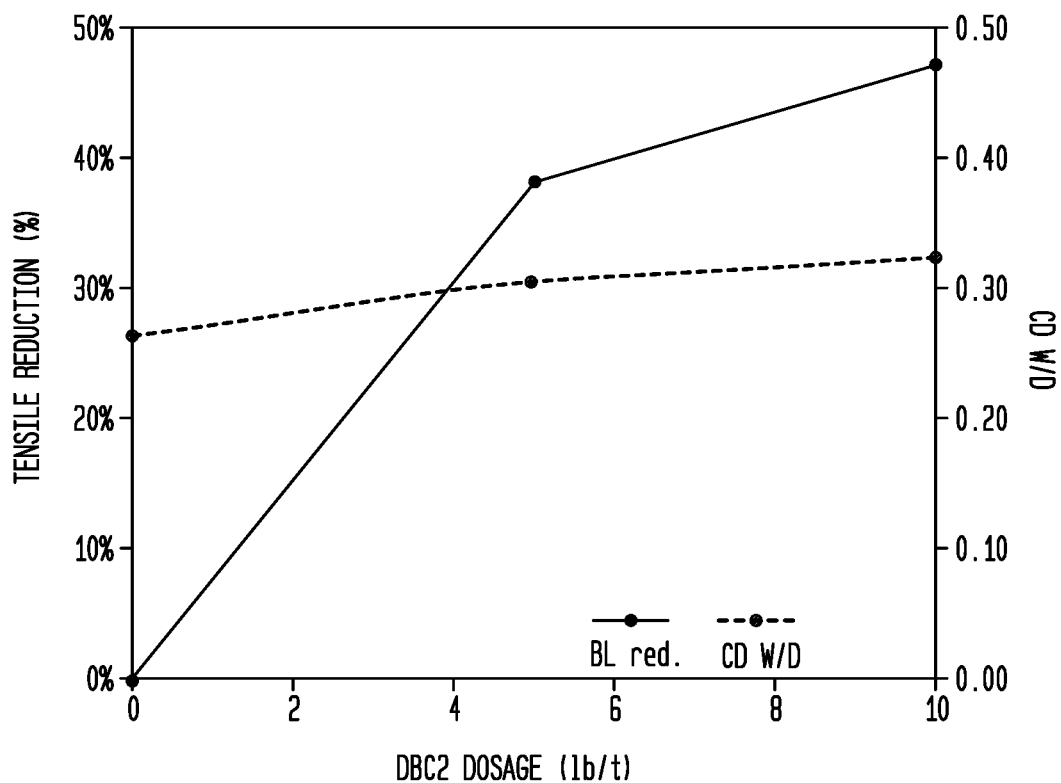
FIG. 6 is a plot of tensile reduction and wet/dry tensile ratios versus debonder dosage for Structured Basesheet, wherein the furnish was treated with debonder, cationic temporary wet strength resin and carboxymethylcellulose.

Tensile results are shown in FIG. 6 wherein it is seen that when Amres® 1110E and CMC were fixed at 12 #/T and 4 #/T respectively, the sheet dosed with DBC2 achieved over 40% dry tensile reduction on the basesheet. Wet/dry tensile ratio was also improved when the furnish was dosed with DBC2.

Summary of Preferred Embodiments

There is thus provided in Embodiment No. 1 a zwitterionic surfactant compound useful for debonder and softener compositions utilized in absorbent paper manufacture, said compound having the formula I:

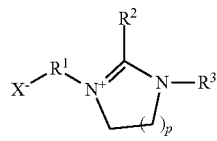

(I)

wherein:

$R^1$ is a straight or branched hydrocarbon spacer moiety having from 2-18 carbon atoms wherein said $R^1$ may be unsubstituted or optionally substituted with one or more groups which can be the same or different and are independently selected from the group consisting of halogen, cyano, alkyl, cycloalkyl, —OH, O($C_1$-$C_6$) alkyl, —C(=O)($C_1$-$C_6$) alkyl, —$CO_2$H, —C(=O)O($C_1$-$C_6$) alkyl, N[($C_1$-$C_6$) alkyl]$_2$, and —NH[($C_1$-$C_6$) alkyl] and/or may have interposed within said hydrocarbon spacer moiety one or more groups which may be the same or different and are independently selected from the group consisting of —NH—C(O)—, —C(O)—NH—, —O—, —$SO_2$— and —C(=O)—;

$R^2$ is a straight or branched saturated or unsaturated hydrocarbon moiety having from 3 to 30 carbon atoms wherein said $R^2$:
  (i) may be unsubstituted or optionally substituted with one or more groups which can be the same or different and are independently selected from the group consisting of halogen, cyano, alkyl, cycloalkyl, —OH, O($C_1$-$C_6$) alkyl, —$CO_2$H, —C(=O)($C_1$-$C_6$) alkyl, —C(=O)O ($C_1$-$C_6$) alkyl, —N[($C_1$-$C_6$) alkyl]$_2$, —NH—C(O)($C_1$-$C_6$) alkyl, —C(O)$NH_2$, —C(O)—NH($C_1$-$C_6$) alkyl, and —NH($C_1$-$C_6$) alkyl, and/or
  (ii) may have interposed within said hydrocarbon moiety one or more groups which may be the same or different and are independently selected from the group consisting of —NH—C(O)—, —C(O)—NH—, —O—, —$SO_2$— and —C(=O)—;

$R^3$ is a straight or branched saturated or unsaturated hydrocarbon moiety having from 3 to 30 carbon atoms wherein said $R^3$:
  (i) may be unsubstituted or optionally substituted with one or more groups which can be the same or different and are independently selected from the group consisting of halogen, cyano, alkyl, cycloalkyl, —OH, O($C_1$-$C_6$) alkyl, —$CO_2$H, —C(=O)($C_1$-$C_6$) alkyl, —C(=O)O ($C_1$-$C_6$) alkyl, —N[($C_1$-$C_6$) alkyl]$_2$, —NH—C(O)($C_1$-$C_6$) alkyl, —C(O)$NH_2$, —C(O)—NH($C_1$-$C_6$) alkyl, and —NH($C_1$-$C_6$) alkyl, and/or
  (ii) may have interposed within said hydrocarbon moiety one or more groups which may be the same or different and are independently selected from the group consisting of —NH—C(O)—, —C(O)—NH—, —O—, —$SO_2$— and —C(=O)—;

wherein at least one of $R^2$ or $R^3$ or has from 8 to 30 carbon atoms;

X is selected from the group consisting of $SO_3$, $CO_2$, $PO_3$ and $HPO_2$; and p is 1 or 2.

Embodiment No. 2 is the zwitterionic surfactant compound of Embodiment No. 1, wherein $R^2$ and $R^3$ have from 8 to 30 carbon atoms.

Embodiment No. 3 is the zwitterionic surfactant compound of Embodiment Nos. 1 or 2, wherein X is $SO_3$.

Embodiment No. 4 is the zwitterionic surfactant compound of Embodiment Nos. 1 or 2, wherein said compound of formula I is an imidazolinium compound of formula II:

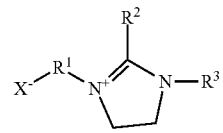

(II)

Embodiment No. 5 is the zwitterionic surfactant compound of Embodiment No. 4, wherein in said compound of formula II, X is $SO_3$.

Embodiment No. 6 is the zwitterionic surfactant compound of Embodiment Nos. 4 or 5, wherein:

$R^1$ is a hydrocarbyl spacer group having a chain length of from 2-6 carbon atoms;

$R^2$ is a hydrocarbyl group having from 8 to 22 carbon atoms; and $R^3$ is an alkenylamidoalkyl moiety having from 8 to 22 carbon atoms.

Embodiment No. 7 is the zwitterionic surfactant compound according to Embodiment No. 6 wherein $R^1$ is an alkylene group of the formula (—$CH_2$—)$_n$ wherein n is an integer from 2 to 6.

Embodiment No. 8 is the zwitterionic surfactant compound according to Embodiment No. 7, wherein n is 3 or 4.

Embodiment No. 9 is the zwitterionic surfactant compound according to any of Embodiment Nos. 4 through 8, wherein $R^2$ is an alkenyl substituent.

Embodiment No. 10 is the zwitterionic surfactant compound according to Embodiment No. 9, wherein $R^2$ is an alkenyl substituent with from 10 to 20 carbon atoms.

Embodiment No. 11 is the zwitterionic surfactant compound according to any of Embodiment Nos. 4 through 10, wherein R3 is an alkenylamidoalkyl moiety of the formula:

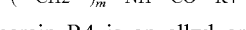

(—CH2—)$_m$—NH—CO—R4 wherein R4 is an alkyl or alkenyl group and m is an integer from 2 to 10.

Embodiment No. 12 is the zwitterionic surfactant compound according to Embodiment No. 11, wherein m is an integer of from 2 to 6.

Embodiment No. 13 is the zwitterionic surfactant compound according to Embodiment Nos. 11 or 12, wherein R4 is an alkenyl substituent having from 10-20 carbon atoms.

Embodiment No. 14 is the zwitterionic surfactant compound according to Embodiment No. 13, wherein R4 is an alkenyl substituent having from 12-18 carbon atoms.

There is provided in Embodiment No. 15 a debonder composition for absorbent paper manufacture comprising a zwitterionic imidazolinium surfactant of any of Embodiment Nos. 1 through 14 in admixture with a nonionic surfactant.

Embodiment No. 16 is the debonder composition according to Embodiment No. 15, wherein the debonder composition comprises from 5 to 45 wt. % of zwitterionic imidazolinium surfactant and from 65 to 95 percent of nonionic surfactant.

Embodiment No. 17 is the debonder composition according to Embodiment Nos. 15 or 16, wherein the debonder composition comprises from 10 to 20 wt. % of zwitterionic imidazolinium surfactant and from 80 to 90 wt. % of nonionic surfactant.

Embodiment No. 18 is the debonder composition according to any one of Embodiment Nos. 15, 16 or 17, wherein the debonder composition comprises a nonionic surfactant selected from alkoxylated fatty acids and alkoxylated fatty alcohols.

Embodiment No. 19 is the debonder composition according to Embodiment No. 18, wherein the debonder composition comprises the reaction product of a fatty acid or fatty alcohol with ethylene oxide.

Embodiment No. 20 is the debonder composition according to Embodiment Nos. 18 or 19, wherein the debonder composition comprises a mixture of mono- and diesters of one or more fatty acids.

Embodiment No. 21 is the debonder composition according to Embodiment No. 20, wherein the mixture of mono- and diesters of the fatty acid(s) are a mixture of PEG monoesters and PEG diesters having a PEG chain molecular weight in the range of 200 to 800.

There is provided in Embodiment No. 22 a method of making absorbent sheet comprising:
(a) preparing an aqueous furnish of papermaking fibers;
(b) incorporating a debonder composition into the aqueous furnish comprising a zwitterionic imidazolinium surfactant of any of Claims 1 through 14;
(c) incorporating a cationic wet strength resin into the aqueous furnish; and
(d) forming the papermaking furnish into absorbent sheet.

Embodiment No. 23 is the method of making absorbent sheet according to Embodiment No. 22, wherein the debonder composition is incorporated into the aqueous furnish prior to incorporating the cationic wet strength resin into the aqueous furnish.

Embodiment No. 24 is the method of making absorbent sheet according to Embodiment No. 22, wherein the cationic wet strength resin is incorporated into the aqueous furnish prior to incorporating the debonder composition into the aqueous furnish.

Embodiment No. 25 is the method according to any one of Embodiment Nos. 22 to 24, wherein the cationic wet strength resin is incorporated into the aqueous furnish at a level of from 2.5 to 30 lbs/ton of papermaking fiber.

Embodiment No. 26 is the method according to any one of Embodiment Nos. 22 to 25, wherein the cationic wet strength resin is incorporated into the aqueous furnish at a level of from 5 to 25 lbs/ton of papermaking fiber.

Embodiment No. 27 is the method according to any one of Embodiment Nos. 22 to 26, wherein the cationic wet strength resin comprises a polyamidoamine epichlorohydrin permanent wet strength resin.

Embodiment No. 28 is the method according to any one of Embodiment Nos. 22 to 26, wherein the cationic wet strength resin comprises a glyoxylated polyacrylamide temporary wet strength resin.

Embodiment No. 29 is the method according to any one of Embodiment Nos. 22 to 28, wherein the debonder composition is incorporated into the aqueous furnish at a level of from 1 to 16 lbs debonder composition per ton of papermaking fiber.

Embodiment No. 30 is the method according to any one of Embodiment Nos. 22 to 28, wherein the debonder composition is incorporated into the aqueous furnish at a level of from 2 to 8 lbs debonder composition per ton of papermaking fiber.

Embodiment No. 31 is the method according to any one of Embodiment Nos. 22 to 28, wherein the debonder composition is incorporated into the aqueous furnish at a level of from 2 to 4 lbs debonder composition per ton of papermaking fiber.

Embodiment No. 32 is the method according to any one of Embodiment Nos. 22 to 31, wherein the debonder composition comprises a zwitterionic imidazolinium surfactant in admixture with a nonionic surfactant.

Embodiment No. 33 is the method according to Embodiment No. 32, wherein the debonder composition comprises from 5 to 45 wt. % of zwitterionic imidazolinium surfactant and from 65 to 95 percent of nonionic surfactant.

Embodiment No. 34 is the method according to Embodiment No. 32, wherein the debonder composition comprises from 10 to 20 wt. % of zwitterionic imidazolinium surfactant and from 80 to 90 wt. % of nonionic surfactant.

Embodiment No. 35 is the method according to any one of Embodiment Nos. 32, 33 or 34, wherein the debonder composition comprises a nonionic surfactant selected from alkoxylated fatty acids and alkoxylated fatty alcohols.

Embodiment No. 36 is the method according to Embodiment No. 35, wherein the debonder composition comprises the reaction product of a fatty acid or fatty alcohol with ethylene oxide.

Embodiment No. 37 is the method according to any one of Embodiment Nos. 32 to 36, wherein the debonder composition comprises a mixture of mono- and diesters of one or more fatty acids.

Embodiment No. 38 is the method according to according to Embodiment No. 37, wherein the mixture of mono- and diesters of the fatty acid(s) are a mixture of PEG monoesters and PEG diesters having a PEG chain molecular weight in the range of 200 to 800.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the foregoing description including the Background of the Invention, the disclosures of which are all incorporated herein by reference, further description is deemed unnecessary. In addition, it should be understood from the foregoing discussion that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A debonder composition for absorbent paper manufacture comprising a zwitterionic imidazolinium surfactant in admixture with a nonionic surfactant, wherein the zwitterionic surfactant has the formula I:

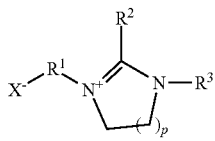

(I)

wherein:
$R^1$ is a straight or branched hydrocarbon spacer moiety having from 2-18 carbon atoms wherein said $R^1$ is unsubstituted or optionally substituted with one or more groups which can be the same or different and are independently selected from the group consisting of halogen, cyano, alkyl, cycloalkyl, —OH, $O(C_1-C_6)$ alkyl, —C(=O)($C_1-C_6$) alkyl, —$CO_2H$, —C(=O)O ($C_1-C_6$) alkyl, N[($C_1-C_6$) alkyl]$_2$, and —NH[($C_1-C_6$) alkyl] and/or optionally have interposed within said hydrocarbon spacer moiety one or more groups which are the same or different and are independently selected from the group consisting of —NH—C(O)—, —C(O)—NH—, —O—, —$SO_2$— and —C(=O)—;
$R^2$ is a straight or branched saturated or unsaturated hydrocarbon moiety having from 3 to 30 carbon atoms wherein said $R^2$:
  (i) may be unsubstituted or optionally substituted with one or more groups which are the same or different and are independently selected from the group consisting of halogen, cyano, alkyl, cycloalkyl, —OH, $O(C_1-C_6)$ alkyl, —$CO_2H$, —C(=O)($C_1-C_6$) alkyl, —C(=O)O($C_1-C_6$) alkyl, —N[($C_1-C_6$) alkyl]$_2$, —NH—C(O)($C_1-C_6$) alkyl, —C(O)$NH_2$, —C(O)—NH($C_1-C_6$) alkyl, and —NH($C_1-C_6$) alkyl, and/or
  (ii) may have interposed within said hydrocarbon moiety one or more groups which are the same or different and are independently selected from the group consisting of —NH—C(O)—, —C(O)—NH—, —O—, —$SO_2$— and —C(=O)—;
$R^3$ is a straight or branched saturated or unsaturated hydrocarbon moiety having from 3 to 30 carbon atoms wherein said $R^3$:
  (i) is unsubstituted or optionally substituted with one or more groups which are the same or different and are independently selected from the group consisting of halogen, cyano, alkyl, cycloalkyl, —OH, $O(C_1-C_6)$ alkyl, —$CO_2H$, —C(=O)($C_1-C_6$) alkyl, —C(=O)O($C_1-C_6$) alkyl, —N[($C_1-C_6$) alkyl]$_2$, —NH—C(O)($C_1-C_6$) alkyl, —C(O)$NH_2$, —C(O)—NH($C_1-C_6$) alkyl, and —NH($C_1-C_6$) alkyl, and/or
  (ii) optionally have interposed within said hydrocarbon moiety one or more groups which are the same or different and are independently selected from the group consisting of —NH—C(O)—, —C(O)—NH—, —O—, —$SO_2$— and —C(=O)—;
wherein at least one of $R^2$ or $R^3$ or has from 8 to 30 carbon atoms;
X is selected from the group consisting of $SO_3$, $CO_2$, $PO_3$ and $HPO_2$; and
p is 1 or 2,
wherein further the nonionic surfactant is selected from alkoxylated fatty acids and alkoxylated fatty alcohols.

2. The debonder composition according to claim 1, wherein the debonder composition comprises from 5 to 45 wt. % of the zwitterionic imidazolinium surfactant and from 65 to 95 wt. percent of the nonionic surfactant.

3. The debonder composition according to claim 2, wherein the debonder composition comprises from 10 to 20 wt. % of the zwitterionic imidazolinium surfactant and from 80 to 90 wt. % of the nonionic surfactant.

4. The debonder composition according to claim 1, wherein the debonder composition comprises a mixture of mono- and diesters of one or more fatty acids.

5. The debonder composition according to claim 4, wherein the mixture of mono- and diesters of the fatty acid(s) are a mixture of PEG monoesters and PEG diesters having a PEG chain molecular weight in the range of 200 to 800.

6. A method of making absorbent sheet comprising:
  (a) preparing an aqueous furnish of papermaking fibers;
  (b) incorporating a debonder composition according to claim 1 into the aqueous furnish;
  (c) incorporating a cationic wet strength resin into the aqueous furnish; and
  (d) forming the papermaking furnish into absorbent sheet.

7. The debonder composition according to claim 1, wherein p is 1.

8. The debonder composition according to claim 1, wherein $R^1$ is a straight or branched hydrocarbon spacer moiety having from 2-18 carbon atoms wherein said $R^1$ are unsubstituted or optionally substituted with one or more groups which are the same or different and are independently selected from the group consisting of halogen, cyano, alkyl, cycloalkyl, —OH, $O(C_1-C_6)$ alkyl, —C(=O)($C_1-C_6$) alkyl, —C(=O)O($C_1-C_6$) alkyl, N[($C_1-C_6$) alkyl]$_2$, and —NH[($C_1-C_6$) alkyl] and/or optionally have interposed within said hydrocarbon spacer moiety one or more groups which may be the same or different and are independently selected from the group consisting of —NH—C(O)—, —C(O)—NH—, —O—, —$SO_2$— and —C(=O)—.

9. The debonder composition according to claim 1, wherein $R^1$ is an alkylene group of the formula (—$CH_2$—)$_n$ wherein n is an integer from 2 to 6.

10. The debonder composition according to claim 9, wherein p is 1.

11. The debonder composition according to claim 1, wherein p is 1 and X is selected from the group consisting of $SO_3$, $PO_3$ and $HPO_2$.

12. The method according to claim 6, wherein p is 1.

13. The method of making absorbent sheet according to claim 12, wherein the debonder composition is incorporated into the aqueous furnish prior to incorporating the cationic wet strength resin into the aqueous furnish.

14. The method of making absorbent sheet according to claim 12, wherein the cationic wet strength resin is incorporated into the aqueous furnish prior to incorporating the debonder composition into the aqueous furnish.

15. The method according to claim 12, wherein the cationic wet strength resin is incorporated into the aqueous furnish at a level of from 5 to 25 lbs/ton of papermaking fiber.

16. The method according to claim 12, wherein the debonder composition is incorporated into the aqueous furnish at a level of from 1 to 16 lbs debonder composition per ton of papermaking fiber.

17. The method according to claim 12, wherein the cationic wet strength resin comprises a polyamidoamine epichlorohydrin permanent wet strength resin.

18. The method according to claim 12, wherein the cationic wet strength resin comprises a glyoxylated polyacrylamide temporary wet strength resin.

* * * * *